United States Patent [19]

Drennan et al.

[11] 4,315,504
[45] Feb. 16, 1982

[54] ELBOW SUSPENSION DEVICE

[75] Inventors: Dennis B. Drennan, Evanston; Donald J. Maylahn, Skokie; Thomas R. Schleicher, Wilmette, all of Ill.

[73] Assignee: DM Systems, Inc., Evanston, Ill.

[21] Appl. No.: 228,102

[22] Filed: Jan. 26, 1981

[51] Int. Cl.³ .............................................. A61B 19/00
[52] U.S. Cl. .................................... 128/149; 128/165
[58] Field of Search .............. 128/149, 165, 132 R, 128/157; 2/24, 16, 239, 240, 241

[56] References Cited

U.S. PATENT DOCUMENTS

| | | | | |
|---|---|---|---|---|
| 2,706,476 | 4/1955 | Diamond | ...................... | 128/149 X |
| 3,322,118 | 5/1967 | Sotherlin | ............................ | 128/149 |
| 3,648,291 | 3/1972 | Pankers | ........................... | 128/165 X |
| 3,990,440 | 11/1976 | Gaylord, Jr. | ....................... | 128/149 |
| 4,150,442 | 4/1979 | Boone | ............................. | 128/165 X |

Primary Examiner—John D. Yasko
Attorney, Agent, or Firm—Mason, Kolehmainen, Rathburn & Wyss

[57] ABSTRACT

An elbow suspension device for bed and ambulatory patients includes a tubular sleeve of flexible material adapted to be slipped onto the arm over the hand and the sleeve is provided with a base portion which is positioned in overlying relation with respect to the bony protuberance of the elbow. A first support pad of resilient foam is mounted in the sleeve on the base portion and includes a central opening adapted to annularly support an outer end portion of the bony protuberance of the elbow and elevate the end or tip of the elbow above the bed surface. A second support pad is mounted on top of the first pad and is also formed of resilient foam. The second pad includes an opening aligned with the opening in the first pad and somewhat larger with a cross-like shape having petal-like segments elongated in a direction longitudinally of the arm and segments elongated in a direction laterally thereof. Edges of the cross-like opening provide support for the arm above and below the elbow and serve to key the support pad to remain firmly in place on the elbow and resist shifting or movement thereof.

22 Claims, 7 Drawing Figures

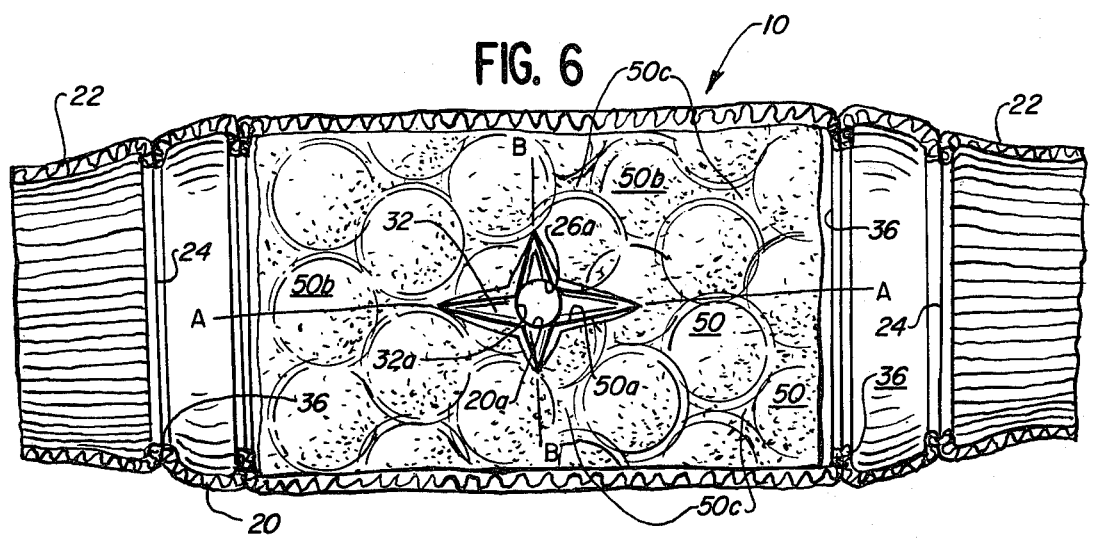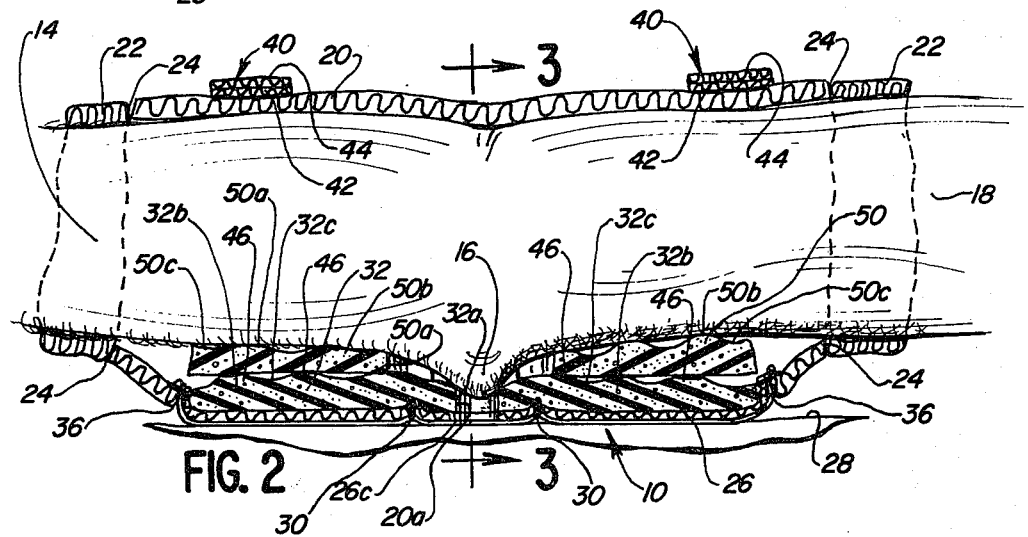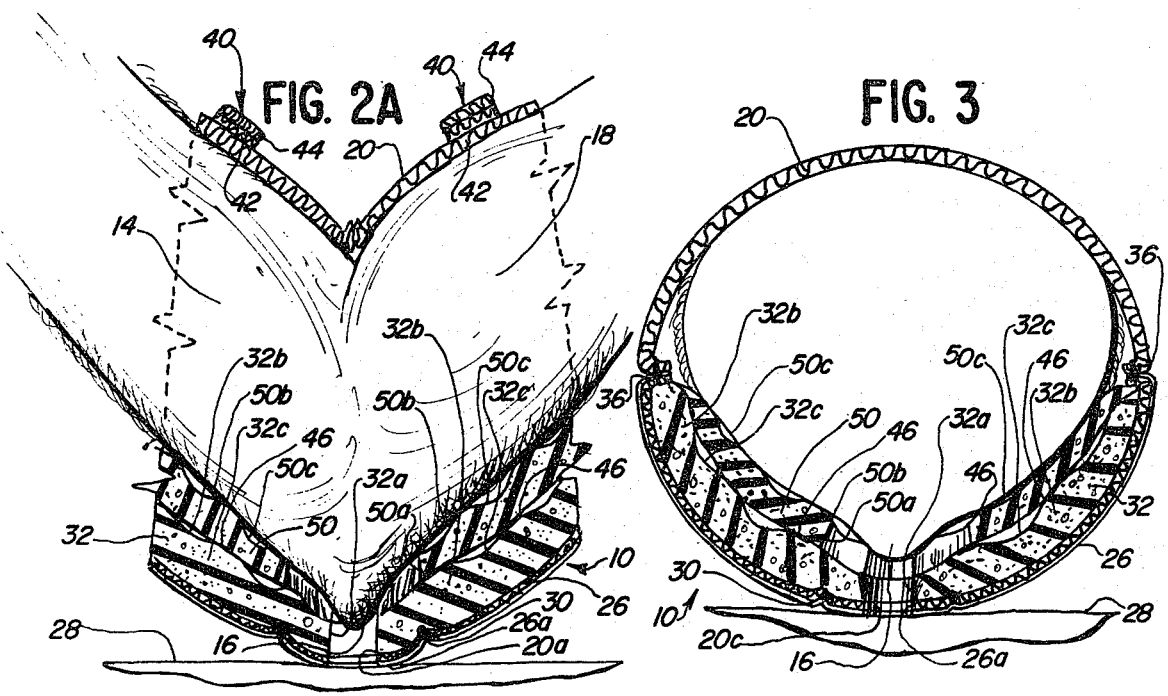

ELBOW SUSPENSION DEVICE

BACKGROUND OF THE INVENTION

Field of the Invention

The present invention relates to a new and improved suspension device for protection of the elbow of bed and ambulatory patients against abrasive contact with bed sheets or other objects. The device is particularly useful for the prevention and treatment of decubitus ulcers which may form on the elbow because of continuous and repeated frictional contact with the bed sheets.

Over the years, a variety of heel and elbow protective devices for bed patients have been developed and the following list of U.S. patents show and describe a variety of prior art protective devices for the heel and elbow:

U.S. Pat. No. 2,550,461—Thick
U.S. Pat. No. 2,986,747—Posey
U.S. Pat. No. 3,216,417—Posey
U.S. Pat. No. 3,322,118—Southerland
U.S. Pat. No. 3,458,867—S. C. Moore et al
U.S. Pat. No. 3,511,233—Holley, Jr.
U.S. Pat. No. 3,606,884—Peter
U.S. Pat. No. 3,648,291—Bankers
U.S. Pat. No. 3,693,619—Williams
U.S. Pat. No. 4,076,022—Walker
U.S. Pat. No. 4,120,062—Buttler
U.S. Pat. No. 4,150,442—Boone
U.S. Pat. No. 4,193,134—Hanrahan Applicants herein have also previously developed a heel supporting boot for bed patients shown and described in U.S. Pat. No. 4,186,738. Many of the existing prior art suspension devices have been subject to a range of difficulties and disadvantages. A major one of these difficulties is the tendency of the support device to come loose from the limb, fall off, or slide and rotate on the limb to a position wherein the elbow or other joint is not supported or protected. Many prior art devices are not designed to accommodate normal patient movement and tend to reduce patient activity when worn. In addition, many of the prior art devices tend to restrict normal movement of the limb and also become hot and uncomfortable to the patient because of inadequate air ventilation adjacent the skin. Other difficulties are encountered with prior art devices including the creation of undesirable high pressure points between the suspension device and the body surface, often resulting in a sore or restriction of circulation. Prior art devices do not allow for convenient treatment of ambulatory patients with such disorders as olecranon bursitis because of slippage.

OBJECTS OF THE INVENTION

It is an object of the present invention to provide a new and improved elbow suspension device and more particularly, a device which eliminates many or all of the difficulties and disadvantages of prior art elbow or heel suspension devices.

More particularly, it is an object of the present invention to provide a new and improved elbow suspension device which is capable of being positively secured in the desired supportive/protective position on the elbow and on which after being placed in position is not easily moved or dislodged by normal patient movement and activity.

Another object of the present invention is to provide a new and improved elbow suspension device of the character described which provides a positive key-like engagement between the elbow supporting portions of the device and the patient's elbow in an arrangement which almost entirely eliminates the problem of shifting or rotation on the patient's arm.

Yet another object of the present invention is to provide a new and improved elbow suspension device which provides annular support around the bony protuberance of the elbow without pressure points or regions of intense or high pressure contact.

Yet another object of the present invention is to provide a new and improved elbow suspension device which permits movement of the elbow over the surface of the bed or sheet without any tendency to catch or bind and thus, affords a patient a greater freedom of movement without any danger of dislodging or moving the suspension device to an improper or ineffective position.

Still another object of the present invention is to provide a new and improved elbow suspension device which is suitable for use with patients of different sex, age and size with the capability of accommodating a wide range of arm sizes.

Another object is to provide a new and improved suspension device of the character described which is simple and easy to put on and take off.

Still another object of the present invention is to provide a new and improved elbow suspension device of the character described which provides for good air ventilation around the skin and yet which is securely fastened in place to provide for a free and full range of motion at the elbow.

Still another object of the present invention is to provide a new and improved elbow suspension device of the character described which is light in weight, relatively small in size, and economical to manufacture.

Still another object of the present invention is to provide a new and improved elbow suspension device which provides for support both of the forearm and the upper arm yet suspends the bony protuberance of the elbow in an annular ring-like area out of contact with the bed cloth.

Yet another object of the present invention is to provide a new and improved elbow suspension device which is useful in the treatment and prevention of decubitus ulcers or bed sores on the elbow of bed patients.

BRIEF DESCRIPTION OF THE DRAWINGS

For a better understanding of the invention, reference should be had to the following detailed description taken in conjunction with the drawings, in which:

FIG. 2 is a longitudinal cross-sectional view taken substantially along lines 2—2 of FIG. 1;

FIG. 2A is a longitudinal cross-sectional view similar to FIG. 2, but showing the suspension device while the patient's arm is bent or flexed at the elbow;

FIG. 3 is a laterally transverse cross-sectional view taken substantially along lines 3—3 of FIG. 2;

FIG. 6 is a longitudinal cross-sectional view taken substantially along lines 6—6 of FIG. 4.

BRIEF SUMMARY OF THE INVENTION

Figure 1:
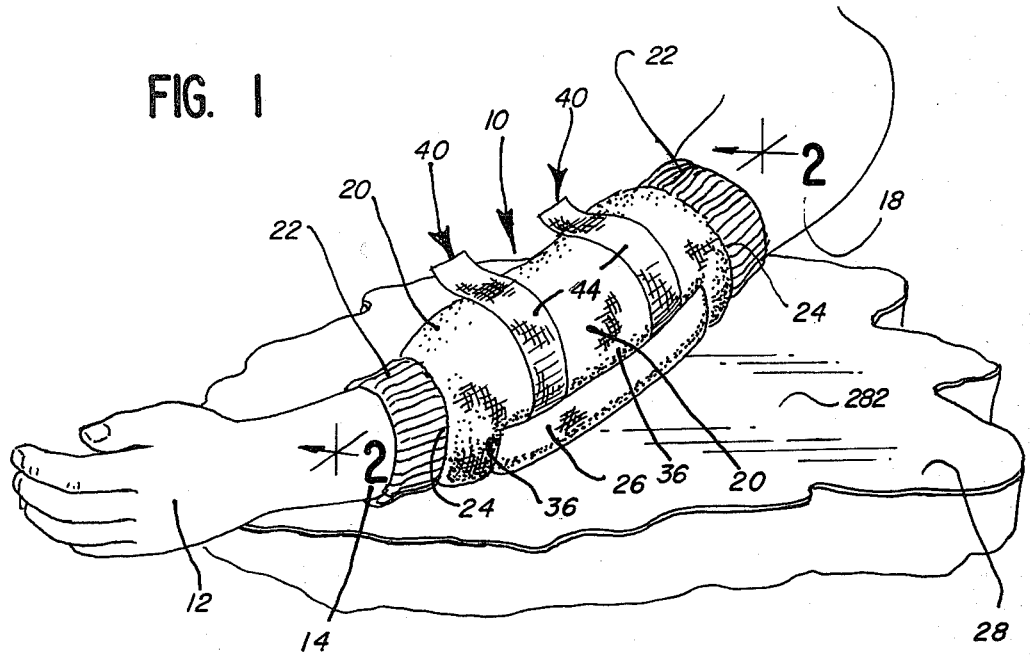
FIG. 1 is a perspective elevational view illustrating a new and improved elbow suspension device constructed in accordance with the features of the present invention and shown as it is worn on the arm of a bed patient.

The foregoing and other objects and advantages of the present invention are accomplished in an illustrated embodiment, by way of representation and not limitation, which embodiment comprises a new and improved suspension device for protection of the elbow against contact with bed sheets and other objects. The device includes a tubular sleeve of flexible material adapted to be slipped onto the arm and having a base portion adapted to be positioned in overlaying relation with respect to the bony protuberance of the elbow. A first support pad of resilient cellular foam is mounted in the sleeve on the base portion and is formed with a central opening to provide annular support for an outer end portion of the bony protuberance of the elbow to elevate the tip of the elbow above the surface of the bed sheet. A second support pad is mounted in the sleeve on the first support pad and is also formed of resilient cellular foam material but with a larger opening overlying the first opening and having a generally cross-shaped configuration elongated in a direction longitudinally of the arm and along a cross-axis extending laterally of the arm. The edges of the openings supportively contact the forearm and upper arm with the elbow in keyed relation extended into the openings of the resilient foam supporting pads.

The suspension device also includes a pair of annular, elastic cuffs at opposite ends of the sleeve to encircle the arm and a base covering of smooth material having a low coefficient of friction to permit easy sliding of the suspension device over a bed sheet or other surface. The device includes a pair of straps adapted to extend around the sleeve both above and below the elbow to aid in securing the sleeve in place against rotation or slippage on the arm. These straps are provided with "Velcro" type fasteners to permit rapid and easy attachment and detachment when securing the elbow suspension device in position on the arm or loosening the device prior to taking it off.

DESCRIPTION OF A PREFERRED EMBODIMENT

Referring now more particularly to the drawings, therein is illustrated a new and improved suspension device for protecting the elbow against abrasive contact with bed sheets and other objects constructed in accordance with the features of the present invention and referred to generally by the reference numeral 10.

The device 10 is especially adapted for the prevention and treatment of decubitis ulcers on the elbow of bed patients, in particular, is useful in elevating the elbow and supporting the same with the bony protuberance at the tip of the elbow up and away from abrasive contact with bed sheets and the like. The device is also especially adapted for the prevention and treatment of olecranon bursitis in the ambulatory patient.

Referring now to FIG. 1, the elbow suspension device is adapted to be slipped onto the arm of a patient over the hand 12 and up the forearm 14 until keyed in place or centered with respect to the elbow 16. The elbow has a somewhat conically shaped, bony protuberance forming the tip or end thereof both when the arm is straight and when the elbow is bent, as best shown in FIGS. 2, 2A and 3. When properly positioned on the elbow, an upper portion of the suspension device extends upwardly onto the upper arm 18 for supporting this portion of the arm and to aid in maintaining the suspension device in proper position on the arm. The elbow suspension device also provides support for the forearm 14 below the elbow.

The suspension device includes an elongated, hollow, tubular sleeve 20, preferably formed of an open weave type, somewhat elastic or stretchable cloth such as chenille to provide for localized air breathing or circulation of air through the body of the sleeve into contact the skin surface of the arm. The chenille cloth of the sleeve is preferably elastic and the sleeve is open at opposite ends to permit the suspension device to slip easily onto the arm and up into a proper position keyed or centered with respect to the elbow 16 with an upper end portion extended over a portion of the upper arm and a lower end portion extending downwardly over an upper end portion of the forearm below the elbow.

At opposite ends, the sleeve is provided with a pair of annular, elastic cuffs 22, preferably of knitted, open weave construction, and these cuffs are secured to opposite ends of the main body of the sleeve by rows of suitable stitching 24. The normal diameter of the cuffs 22 is somewhat smaller than that of the sleeves to provide a relatively secure fit on the arm and the elastic property of the sleeve and cuffs permits one size of suspension device 10 to be used for a wide range of arm sizes.

In accordance with the invention, the sleeve 20 is provided with an outer base section 26 of generally rectangular shape formed of a separate piece of cloth. The cloth is preferably of an open weave type material having a relatively smooth outer surface texture such as acetate so that the suspension device 10 may slide easily and smoothly over the surface of a bed sheet 28 or other external surface with a minimum of difficulty. The base segment is formed with a circular opening 26a at the center thereof aligned with a similarly shaped opening 20a formed in the cloth at the bottom of the sleeve body. Around the openings 20a and 26a, the base 26 and outer surface of the sleeve 20 are secured together by an annular ring of adhesive 30 aligned in concentric relationship with the smaller central openings. The smooth outer surface of the acetate base 26 prevents the body of the sleeve from wrinkling or binding when the suspension device 10 is moved to slide over a surface of a bed sheet 28. The smooth base also provides little or no interference or restriction of movement of the device and the position of the device on the arm of a patient does not readily change, such as by sliding or rotating on the arm of the patient.

In accordance with the present invention, the elbow suspension device includes a generally rectangular, lower cushion or support pad 32 formed of resilient, cellular foam material of substantial thickness to support the bony protuberance 16 of the patient's elbow in an elevated position with the tip of the elbow suspended above and out of contact with the surface of the bed sheet 28, both when the arm is in a relatively straight condition as shown in FIG. 2 and while the elbow is bent as shown in FIG. 2A.

The resilient, cellular foam material of the lower support pad 32 is formed with a circular opening 32a concentrically aligned with the circular openings 20a and 26a of the sleeve and base, respectively.

The upwardly facing surface of the support pad 32 is formed with a plurality of shallow alternate peaks 32b and valleys 32c and this type of surface provides a plurality of diverse air passages for air circulation over the upper surface of the support pad. The upper edges of the pad around the central opening are compressible and provide an annular support ring for the elbow with a relatively low and substantially uniform pressure around the entire elbow but spaced away from the tip. The foam pad is compressed by the pressure of the elbow when the elbow is extended into the circular opening and the elbow is supported as if positioned in a soft "doughnut"-shaped cushion in the pad 32 with the tip of the elbow suspended in the open air.

Around the entire rectangular perimeter of the pad, a line of stitching 36 is provided to fasten the pad in place in the sleeve 20 and this line of stitching also fastens the outer edges of the acetate base sheet 26 to the body of the sleeve. Parallel rows of stitching 36 along opposite longitudinal sides of the base 26 also fasten the ends of a pair of holding straps or belt-like adjustable length loops 40 which extend in a transverse direction around the exterior of the sleeve. The straps are positioned on longitudinally opposite sides of the central opening 32a in the support pad 32 above and below the elbow of the arm.

The belt-like straps 40 may be tightened as needed around the sleeve 20 to aid in positively securing the sleeve in place in the proper position on the forearm and the upper arm of the patient. Easy belt assembly includes a first strap 42 attached to one edge of the acetate base 26 and provided on an upper surface thereof with a plurality of small filamentary hook or loop elements of the type known as "Velcro" fasteners. A second strap 44 is attached to the opposite side of the base and is provided with a plurality of small, filamentary loop or hook elements on an inner surface thereof adjacent an outer end portion. In each strap assembly 40, the hooks of one strap are detachably engageable with the loops on the other strap to provide an easy means for adjusting the tightness of the strap assembly around the sleeve. The pair of straps provide means for more positively fixing the position of the sleeve 20 on the arm and the straps are adjustable so that excessive pressure is not exerted on the skin surface of the forearm or upper arm. The "Velcro" type hook and loop fastening elements are shown and described in U.S. Pat. No. 3,748,701 and are not described in detail herein except that these type of fastening devices are well adapted to be used with the strap assemblies 40 to provide a comfortable, yet firm placement of the device on the arm of the patient.

In accordance with the present invention, the elbow suspension device 10 also includes a second, generally rectangular, upper support pad 50 of resilient cellular foam material which is mounted on and secured to the upper surface of the lower support pad 32. The upper pad is mounted in the sleeve 20 and is secured to the lower pad with a plurality of spots of adhesive material 46 provided on the peaks 32b. The adhesive spots attach the relatively flat undersurface of the upper pad 50 in place at a plurality of points which comprise a grid-like matrix of fastening points between the upper and lower foam pads. This fastening arrangement permits limited relative shifting between the pads 32 and 50 in a limited amount and minimizes movement of the pad 50 relative to the surface of the skin.

Figure 4:
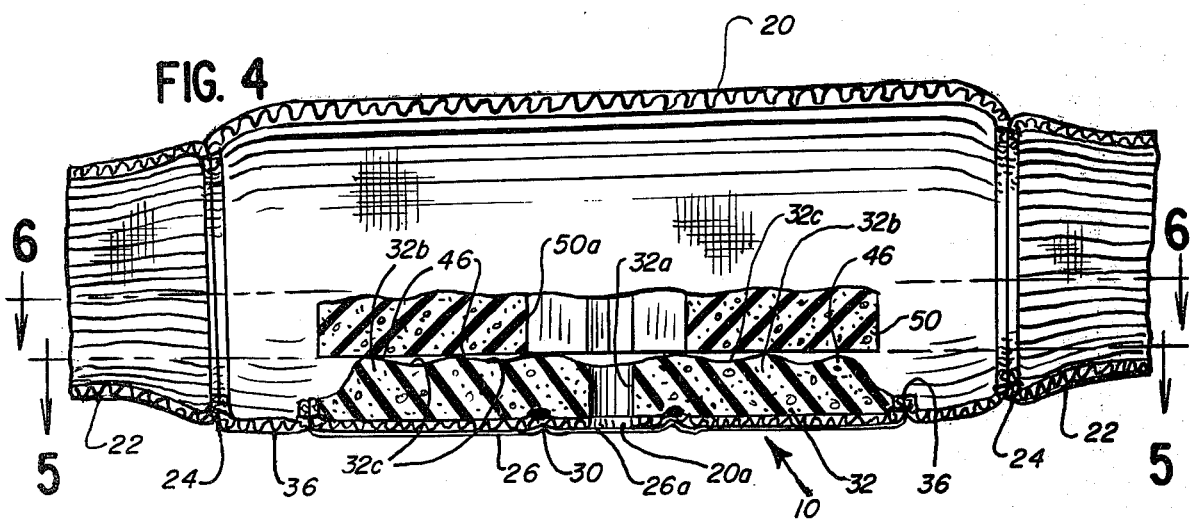
FIG. 4 is a longitudinal cross-sectional view showing the suspension device in accordance with the features of the present invention in an open condition ready to be slipped onto the arm of a bed patient.
Figure 5:
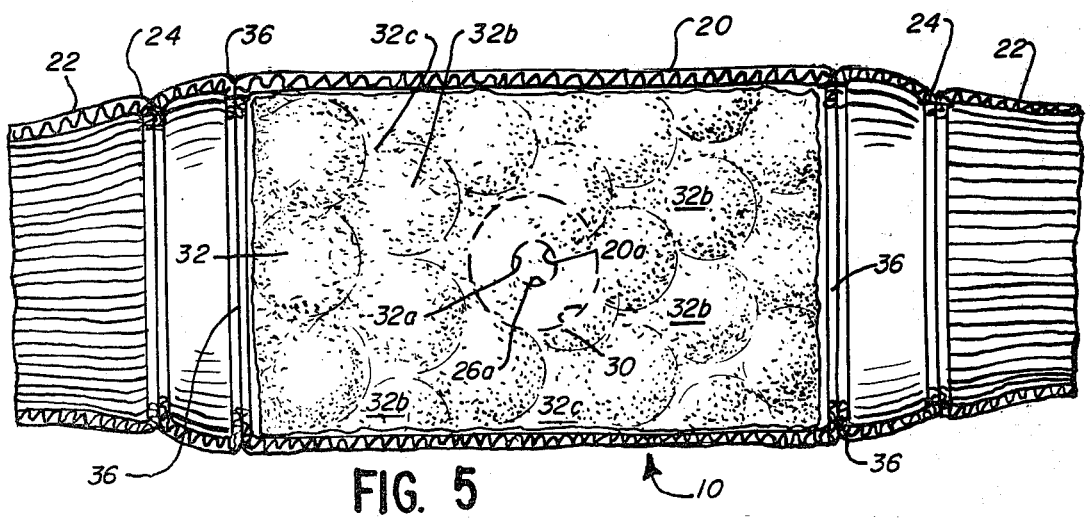
FIG. 5 is a longitudinal cross-sectional view taken substantially along lines 5—5 of FIG. 4.

As best shown in FIGS. 4 and 6, the upper support pad 50 is formed with a cross-like or four point star shaped opening 50a that is larger than and aligned in coaxial alignment with the circular opening 32a of the lower pad 32. The upper surface of the upper pad is formed with a plurality of alternate peaks and shallow valleys 50b and 50c like those of the lower pad and the valleys provide diverse plural paths for air circulation around the surface of the skin just as the valleys 32c permit circulation of air between the respective upper and lower pads. Preferably, the foam material of the pads 32 and 50 is an open celled type and is non allergenic.

The grid-like matrix or spacing between the peaks 50b of the upper pad 50 provides low pressure support of the arm of the patient at a plurality of spaced apart locations within the sleeve and thus tends to eliminate the concentration of pressure at a single point of high stress which would tend to cause abrasion or sores. In addition, the gentle, undulating upper surface of the upper support pad 50 provides support over an extensive area of the arm both below and above the elbow and permits the free circulation of air so that the sleeve does not become excessively hot during wear.

In accordance with an important feature of the present invention, the upper edges of the lower support pad 32 around the circular shaped central opening 32a provide a doughnut-like, annular supporting surface around the bony protuberance 16 of the elbow to support the tip of the elbow spaced above and away from the bed sheet 28 or other surface on which the sleeve is laying. This gentle, low pressure support around an annular area encircling the tip of the elbow, permits a good circulation of air around the elbow to promote healing. This supportive engagement may be likened to that of a loose fitting key and slot engagement and is an important feature in securing and continuously retaining the sleeve 20 in the proper position with respect to the elbow even though the arm may be moved and flexed from the straight position of FIG. 2 to the bent position of FIG. 2A.

Referring to FIGS. 2, 2A and 6, the upper edges of the pad 50 around the cross-shaped opening 50a provide additional key and slot type engagement between the pad 50 and the elbow and additional low pressure support for the forearm 14 and the upper arm 18, generally along the longitudinal axis of the arm as indicated by a line A—A (FIG. 6). Support is also provided along a lateral axis B—B generally normal to the length of the arm. The cross-shaped opening 50a is formed with four (4), elongated, petal-shaped segments, each having a maximum width adjacent the central portion at the opening and with a width tapering towards a minimum value at a pointed outer end. The upper edges of the pad 50 along the outlines of each longitudinally extended, petal-shaped segment is compressed on contact with the arm and supportively engages and cushions skin surfaces on the forearm and the upper arm along the axis A—A.

In similar fashion, the laterally extending petal-shaped segments which extend outwardly in opposite directions along the axis B—B also define compressible upper edge portions which engage and support the surface of the arm laterally with respect to the bony protuberance 16 of the elbow. This supportive and cushioning contact between the upper edges of the pad 50 around the cross-shaped opening 50a and the surface of the skin provides a key-like interlocking relation between the sleeve 20 and the elbow of the patient, yet permits the arm to be flexed in a more or less normal fashion without substantial shifting of the position of the suspension device 10 on the arm.

In the flexed arm position of FIG. 2A, the upper edges of the laterally extending petal-shaped segments of the pad opening 50a tend to move closer together and thus permit the foam pad to flex more freely about the lateral axis B—B. The combination of the uniquely shaped opening 50a in the upper foam pad 50 and the circular opening 32a of the lower support pad 32 provides a positive but low pressure supportive contact around the patient's elbow and suspends the tip of the elbow in an elevated position above the bed sheet 28. The keyed engagement of the elbow in the pad openings 32a and 50a resists and prevents rotation of the sleeve on the arm and prevents unwanted longitudinal movement of the sleeve up or down on the arm.

Although the present invention has been described with reference to a single illustrated embodiment thereof, it should be understood that numerous other modifications and embodiments can be devised by those skilled in the art that will fall within the spirit and scope of the principles of this invention.

What is claimed as new and desired to be secured by Letters Patent of the United States is:

1. A suspension device for protection of the elbow against contact with bed sheets and other objects, comprising:
   a tubular sleeve of flexible material adapted to be slipped onto the arm and having a base portion adapted to be positioned in overlaying relation with respect to the bony protuberance of the elbow;
   a first support pad in said sleeve mounted on said base portion and formed of resilient cellular foam with a central opening adapted to annularly support an outer end portion of the bony protuberance of the elbow spaced from said base; and
   a second support pad in said sleeve mounted on said first support pad and formed of resilient cellular foam with an opening overlying the opening of said first support pad, said opening of said second pad being elongated outwardly with respect to said central opening of said first support pad in a direction extending longitudinally of the arm and having edges for supportive contact with the arm.

2. The suspension device of claim 1 wherein said opening of said second support pad includes a segment tapered from a maximum width adjacent said central opening of said first support pad toward a minimum at a position spaced up the arm toward the shoulder for supportive contact of the arm away from the outer end of the elbow.

3. The suspension device of claim 1 or 2 wherein said opening of said second support pad includes a segment tapered from a maximum width adjacent said central opening of said first support pad toward a minimum at a position spaced down the arm toward the hand for supportive contact of the arm away from the outer end of the elbow.

4. The suspension device of claim 1 wherein said opening of said second support pad is elongated with respect to said central opening of said first support pad in a direction laterally of the arm having edges for supportive contact laterally of the end portion of the elbow.

5. The suspension device of claim 4 wherein said opening of said second support pad includes a segment tapered from a maximum width adjacent said central opening of said first support pad toward a minimum spaced laterally outwardly thereof.

6. The suspension device of claim 4 and 5 wherein said opening of said second support pad is elongated laterally in opposite directions outwardly of said central opening of said first support pad and tapers from a maximum width adjacent said central opening to minimum widths laterally outwardly thereof.

7. A suspension device for protection of the elbow against contact with bed sheets and other objects, comprising:
   a tubular sleeve of flexible material adapted to be slipped onto the arm and having a base portion in overlaying relation with respect to the bony protuberance of the elbow;
   a first support pad in said sleeve mounted on said base portion and formed of resilient cellular foam with a central opening adapted to annularly support an outer end portion of the bony protuberance of the elbow spaced from said base; and
   a second support pad in said sleeve mounted on said first support pad and formed of resilient cellular foam with an opening overlying the opening of said first support pad, said opening of said second pad being elongated with respect to said central opening of said first support pad in a direction extending laterally of said arm and having edges for supportive contact with the arm.

8. The suspension device of claim 7 wherein said opening of said second support pad includes a segment tapered from a maximum width adjacent said central opening of said first support pad toward a minimum at a position spaced laterally outwardly across the arm away from the outer end of the elbow.

9. The suspension device of claim 1 or 8 wherein said opening of said second support pad includes a segment extending in a direction opposite said first mentioned segment tapered from a maximum width adjacent said central opening of said first support pad toward a minimum at a position spaced laterally outwardly across the arm away from the outer end of the elbow.

10. The suspension device of claim 7 wherein said opening of said second support pad is elongated with respect to said central opening of said first support pad in a direction longitudinally of the arm having edges for supportive contact with the arm toward the hand and shoulder away from the end portion of the elbow.

11. The suspension device of claim 1 or 7 wherein said first support pad is secured to said base of said sleeve by stitching around the periphery thereof.

12. The suspension device of claim 11 wherein said first support pad is secured to the base of said sleeve in a ring around said central opening.

13. The suspension device of claim 11 wherein said first support pad has a support surface facing away from said base formed with a plurality of alternate peaks and valleys therein.

14. The suspension device of claim 13 wherein said second support pad is adhesively secured with at least some of said peaks of said first support pad.

15. The suspension device of claim 1 or 7 wherein said second support pad has a support surface facing away from said base formed with a plurality of alternate peaks and valleys therein.

16. The suspension device of claim 1 or 7 including a layer of flexible material on said base of said sleeve having a low coefficient of friction for smooth sliding contact with a bed sheet or the like.

17. The suspension device of claim 1 or 7 wherein said sleeve is provided with a pair of elastic cuffs at opposite ends for annular contact around the arms above and below the elbow.

18. The suspension device of claim 1 or 7 wherein said sleeve material has a plurality of openings therein permitting air passage into said sleeve for contact with the arm.

19. The suspension device of claim 18 wherein said sleeve material is elastic.

20. The suspension device of claims 1 or 7 including at least one belt means of adjustable length for encircling said sleeve around the arm remote from the elbow for securing said sleeve in place on the arm.

21. The suspension device of claim 20 including a plurality of said belt means around said sleeve spaced on opposite sides of said opening in said first support pad up and down the arm from the elbow.

22. The suspension device of claim 20 wherein said belt means includes a "Velcro" type detachable fastening system for adjusting the effective length thereof.

* * * * *